United States Patent [19]

Khacdung

[11] Patent Number: 4,916,753
[45] Date of Patent: Apr. 17, 1990

[54] SAFETY WELDING MASK

[76] Inventor: Do Khacdung, 33 High St., Apt. #22, Orange, N.J. 07050

[21] Appl. No.: 282,746
[22] Filed: Dec. 12, 1988
[51] Int. Cl.⁴ ............................................. A61F 9/06
[52] U.S. Cl. ............................................................ 2/8
[58] Field of Search ................. 2/8, 432, 424; 219/147

[56] References Cited
U.S. PATENT DOCUMENTS

| | | | |
|---|---|---|---|
| 3,339,207 | 9/1967 | Perry | 2/8 |
| 3,833,936 | 9/1974 | Lo Guidice | 2/8 |
| 4,525,876 | 7/1985 | Bailey | 2/8 |
| 4,546,498 | 10/1985 | Fantin | 2/8 X |
| 4,679,255 | 7/1987 | Kuhlman | 2/8 |
| 4,686,711 | 8/1987 | Budmiger | 2/8 |

Primary Examiner—Peter Nerbun
Attorney, Agent, or Firm—Leon Gilden

[57] ABSTRACT

A safety welding mask is set forth provided with a self-contained battery power supply and associated switching for opening and closing of a safety window associated with the welding mask.

1 Claim, 3 Drawing Sheets

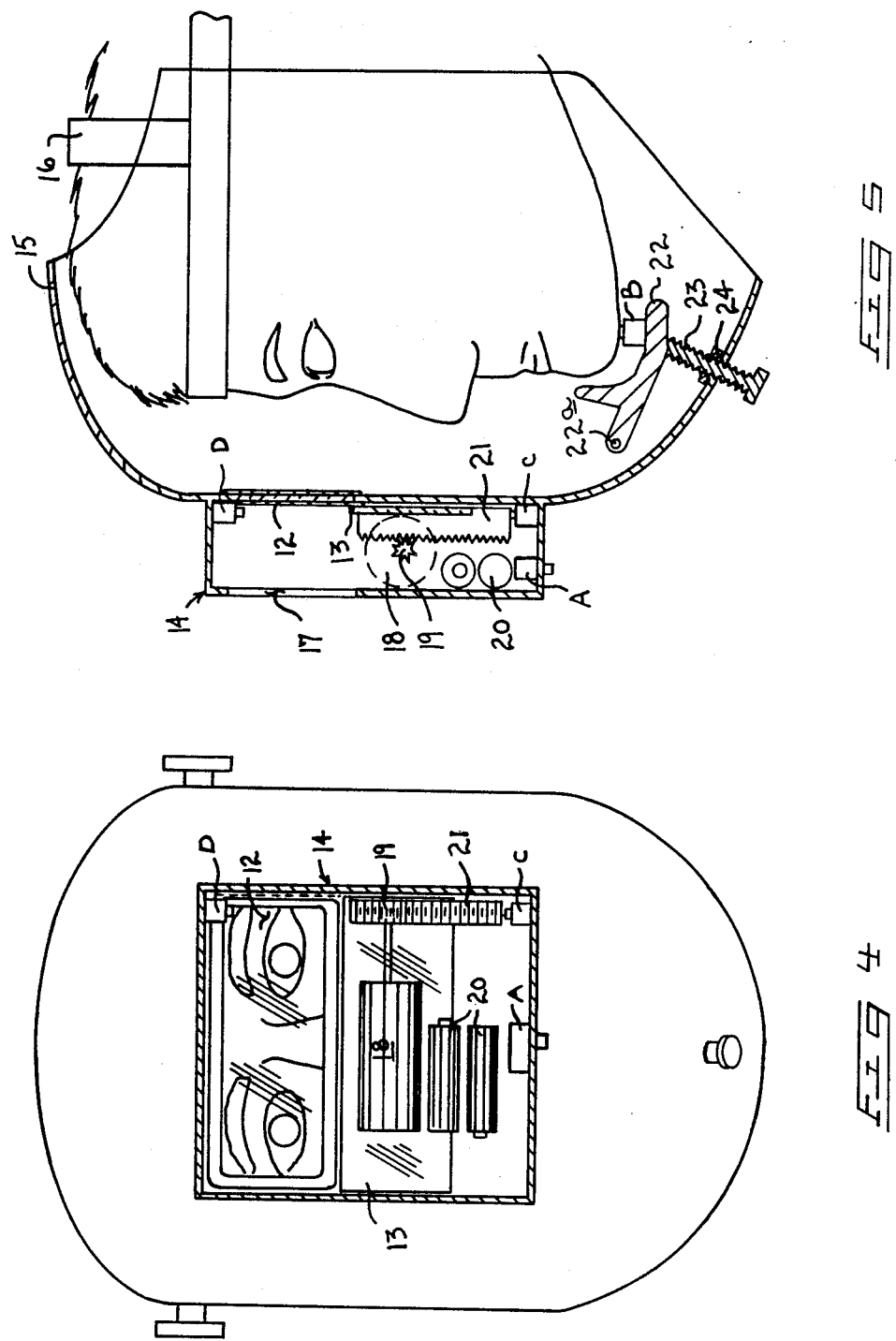

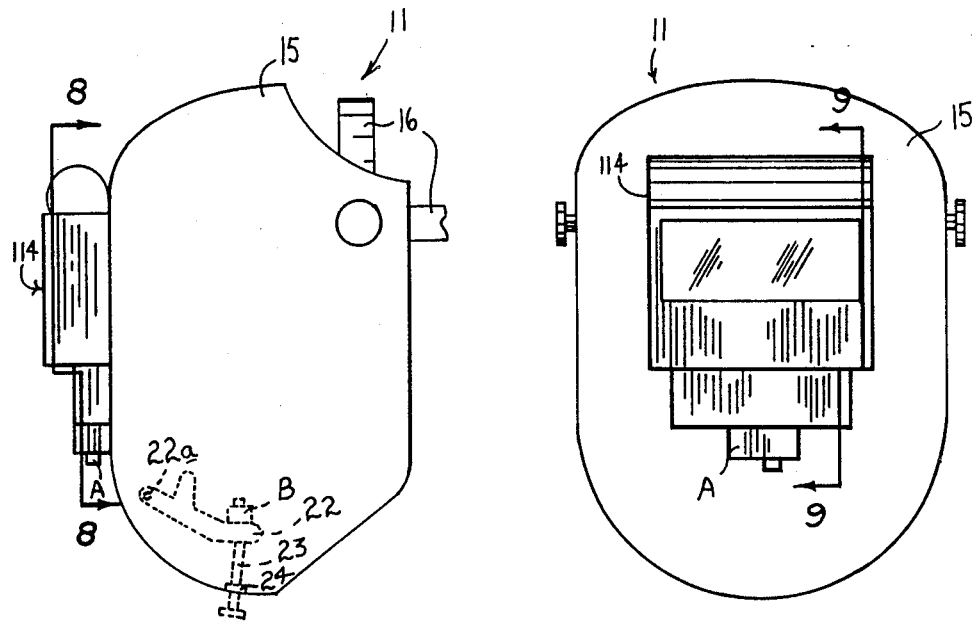
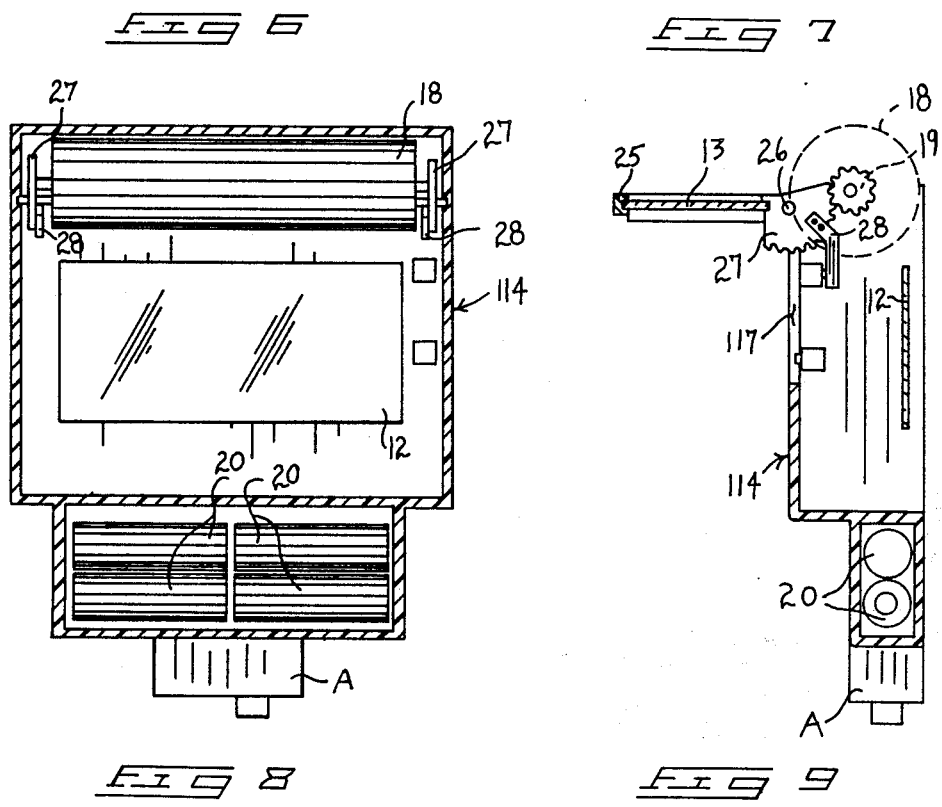

SAFETY WELDING MASK

BACKGROUND OF THE INVENTION

1. Field of the Invention

The field of invention relates to welding masks, and more particularly pertains to a new and improved safety welding mask provided with motorized mechanisms to open and close a safety window associated with a safety mask including a chin operatively actuated opening switch.

2. Description of the Prior Art

The use of welding safety masks or hoods is well known in the prior art. Typically such masks are provided with a safety window to provide a line of sight for an operator to view a welding operation. Conventionally, a tinted glass protects a user's eyes from the high energy arcs generated during a welding operation. There have been several attempts to develop chin operated safety mask devices for use in a welding operation of mechanical linkage. Mechanical linkage, unfortunately, is subject to binding and deterioration by airborne contaminants that tend to erode the efficiency and operatives of such devices. A first example of a chin operated safety mask is available in U.S. Pat. No. 8,517,892 to Hodge wherein a flexible chin strap is operably secured to a plural linkage to open an associated window upon lowering of a chin and is provided with a spring biased mechanism to close the window upon repositioning of a wearer's chin. The device is typical of the mechanisms utilized in such devices.

U.S. Pat. No. 4,694,507 to Owen sets forth a further mechanism for opening and closing a window closure of a welder's helmet by use of a plurality of linkages and arms that ultimately engages a wearer's chin and as in the Hodge patent, is provided with a spring return for closure of the associated window.

U.S. Pat. No. 4,589,713 to Hodge sets forth a further welding hood and a chin operated linkage arrangement wherein a variation of a chin operated linkage is set forth utilizing a spring means to bias the shield to a closed orientation.

U.S. Pat. No. 4,525,876 to Bailey utilizes a further variation of linkages and the like to enable the use of a plurality of filters to vary the filtering effects of the helmet to protect a wearer against very intensities of light generated during a welding procedure.

U.S. Pat. No. 8,775,774 to Herman sets forth a further example of a welding helmet with a spring bias means to normally bias a lens to position over a lens opening of a associated helmet with included chin linkage means to move that lens away from the opening, as desired by the operator.

Prior inventions have included the same disadvantage requiring the welder to keep his mouth open during a welding procedure enabling foreign debris to enter the welder's mouth and further imparting fatigue. The instant invention only requires the welder to lower his chin once to operate a switch to open or to close associated safety glass.

As such, it may be appreciated that there is a continuing need for a new and improved safety welding mask that enables the use of electrical components to easily and efficiently effect the opening and closing of a window lens over a window lens in an associated welding mask.

SUMMARY OF THE INVENTION

In view of the foregoing disadvantages inherent in the known types of welding masks no present in the prior art, the present invention provides a safety welding mask wherein the same may be operative to easily and efficiently position a lens cover over a lens opening in the welding mask motivated by electrical means. As such, the general purpose of the present invention, which will be described subsequently in greater detail, is to provide a new and improved safety welding mask which has all the advantages of the prior art welding masks and none of the disadvantages.

To attain this, the present invention comprises a self-contained power supply and associated switching operative to actuate an associated motor and linkage arrangement to pivotally manipulate a lens covering over lens opening in a first embodiment or reciprocatably position into and out of orientation over a lens opening, a lens relative to a lens opening in a welding mask.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved safety welding mask which has all the advantages of the prior art safety welding masks and none of the disadvantages.

It is another object of the present invention to provide a new and improved safety welding mask which may be easily and efficiently manufactured and marketed.

It is a further object of the present invention to provide a new and improved safety welding mask which is of a durable and reliable construction.

An even further object of the present invention is to provide a new and improved safety welding mask which is susceptible of a low cost of manufacture with regard to both materials and labor and which accordingly is then susceptible of low prices of sale to the consuming public, thereby making such safety welding masks economically available to the buying public.

Still yet another object of the present invention is to provide a new and improved safety welding mask which provides in the apparatuses and methods of the prior art some of the advantages thereof, while simultaneously overcoming some of the disadvantages normally associated therewith.

Still another object of the present invention is to provide a new and improved safety welding mask that enables the use of a self-contained battery pack to operate a reversible motor to selectively open and close a lens covering over a lens opening in a welding mask.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. I is a side orthographic view of a welding mask as utilized by the instant invention.

FIG. 4 is a frontal orthographic view of the instant invention illustrating the rack and pinion mechanism to reciprocate a lens covering relative to a lens opening in the instant invention.

FIG. 5 is an orthographic side view of the instant invention illustrating the rack and pinion arrangement to reciprocate a lens covering relative to a lens opening in the instant invention.

FIG. 6 is a side orthographic view of the modification of the instant invention.

FIG. 7 is a frontal orthographic view of a modification of the instant invention as set forth in FIG. 6.

FIG. 8 is an orthographic view taken along the lines 8—8 of FIG. 6 in the direction indicated by the arrows.

FIG. 9 is an orthographic view taken along the lines 9—9 of FIG. 7 in the direction indicated by the arrows.

DESCRIPTION OF THE PREFERRED EMBODIMENT

Figures 1, 2:
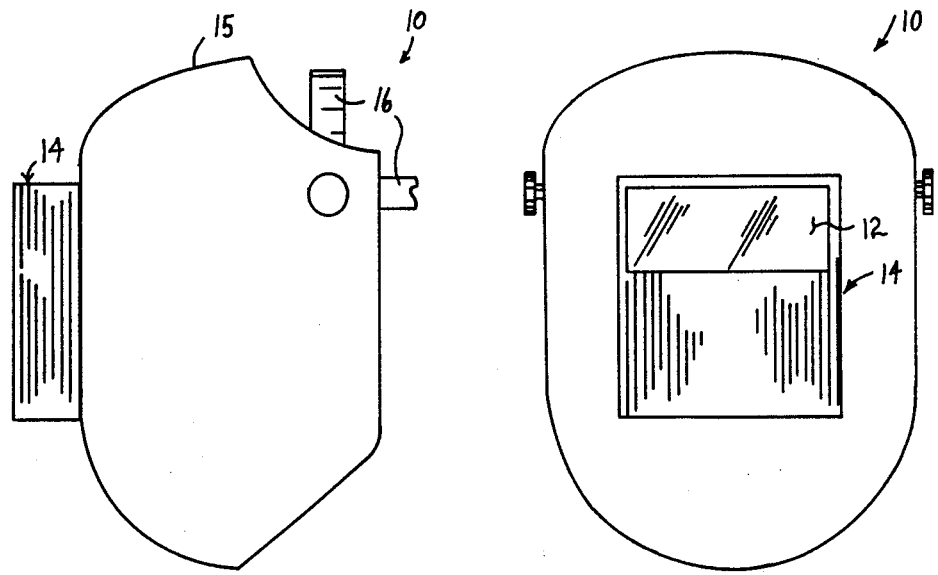
FIG. 2 is a front orthographic view of a welding mask typically utilized by the instant invention.

With reference now to the drawings, and in particular to FIGS. 1 to 9 thereof, a new and improved safety welding mask embodying the principles and concepts of the present invention and generally designated by the reference numerals 10 and 11 will be described.

More specifically, it will be noted that the safety welding mask 10, as set forth in FIGS. 1 through 5, essentially comprises a conventional welding mask including a hood 15 with a plurality of securement straps 16 thereto for positioning about a user's head. A forwardmost framework 14 overlies a clear impact resistant window 12 fixedly mounted within the framework 14 in alignment with the outer peripheral surface of the hood 15, as illustrated in FIG. 5 for example. A forwardmost opening 17 is formed in alignment with the impact resistant window 12 and is formed in a forwardmost portion of the box-like framework 14. In use, it is desired for a colored lens 13 to be positionable overlying the window 12 to minimize damage to a user's eyes by the arcing of the welding procedure. To this end, a motor 18 is mounted with an axially extended gear drive 19 cooperating with a rack 21 that is fastened fixedly to the colored lens 13.

It is desired to elevate and lower the colored lens 13 relative to the opening 17 and the window 13, and to this end a plurality of batteries 20 is positioned underlying the opening 17 within the framework 14 and electrically powering the motor 18 to raise and lower the lens.

Figure 3:
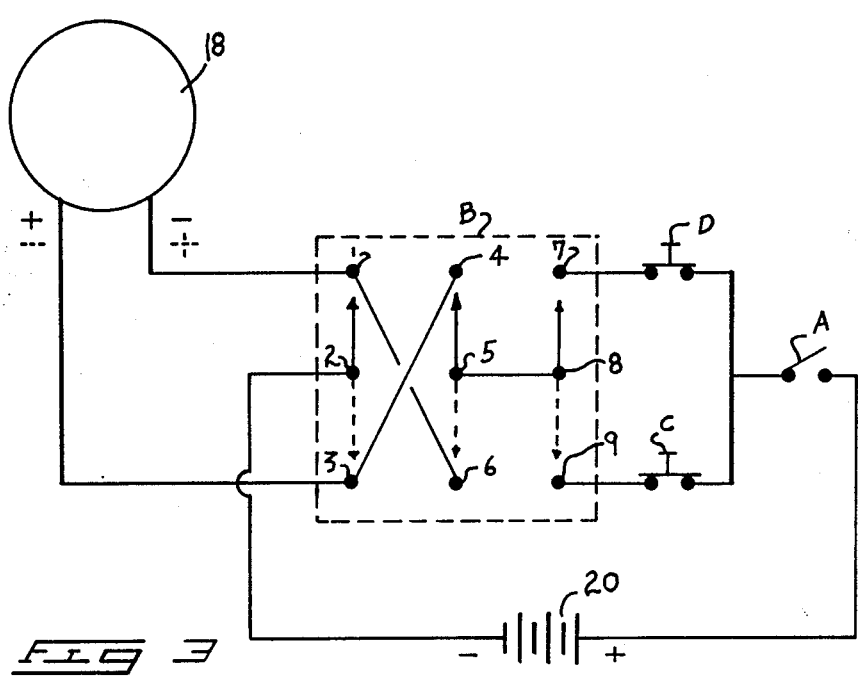
FIG. 3 is a diagrammatical representation of electrical circuitry utilized by the instant invention.

Reference to FIG. 3 sets forth the cooperation of the batteries 20 to the motor 18. A first switch "A" positioned for manual operation at a lowermost portion of the framework 14 cooperative with a triple pole, double throw "push-type" switch "B" positioned upon a pivoted support 22 that is mounted for pivotment upon a pivot 22a. The pivoted support 22 is adjustable by means of an adjustment shaft 23 that is externally threaded and adjustable axially within an internally threaded boss 24, as illustrated in FIG. 5. The adjustment shaft 23 is secured to the support 22 to carry the support 22 as the shaft 23 is retracted and extended through the threaded boss 24.

Upon actuation of the switch "A", the triple pole, double throw switch "B" is in a first position with the associated lens 13 at a bottom position, as set forth by the solid arrows in FIG. 3, whereupon current from the batteries 20 is directed through switch "A", then through switch "D" as it remains in a normally closed position per FIG. 5 and FIG. 3, and thereupon electrical current is directed through terminals 7, terminal 8, terminal 5, terminal 4, and terminal 3 to motor 18 and thereafter directed through respective terminal 1 and 2 back to the battery supply 20 to complete the direct current circuit whereupon motor 18 is energized, turns piston 19 to direct rack 21 and attached lens 13 upwardly. Upon the lens 13 reaching its upper limit of travel, the uppermost edge of lens 13 comes into contact with the switch "D" opening switch "D" and shutting off power to the motor 18. It should be noted that switch "D" is a limit switch, normal closed, push type,. on-off switch.

Subsequent to a welding operation, and upon an operator's desiring to lower lens 13, the operator merely actuates switch "B" to the second or dotted position, as illustrated in FIG. 3, by use of the operator's chin, as illustrated in FIG. 5. Thereupon, electrical current will be directed from the batteries 20 through the switch "A", switch "C", then through terminal 9, terminal 8, terminal 5, terminal 6, then through terminal 1 to the motor 18 whereupon the motor will reverse polarity, as illustrated in the phantom polarity reversal designation, and flow from the motor to terminal 3 then to terminal 2 which is again directed back to the battery source wherein motor 18 is energized to reverse direction to lower lens 13, and upon the lens reaching its lowermost extent of travel, switch "0" is opened stopping the motor 18. It should be noted that switch "C" is a normally closed "push-type" on/off switch, and it is a limit switch.

It may thus be appreciated that the colored lens 13 will be automatically and electrically reciprocated upwardly and downwardly by means of the application of power from motor 18 to the rack 21 that is secured integrally to the lens 13 with a minimal of physical effort by an operator that merely impinges upon the switch "B" by use of his chin.

Similarly, the modification, as st forth in FIGS. 6 through 9, is operative in a like manner by the use of the same circuitry, as illustrated in FIG. 3.

A framework 114 is provided with an opening 117, as illustrated in FIG. 9, with a colored lens 18 pivotal upwardly and downwardly to selectively overlie and cover the opening 117.

The framework 114 is in this instance formed with a pivoting frame 25 at an uppermost position relative to the opening 117 and formed with a similar colored lens 13 that is pivoted about pivot point 26. An arcuate gear 27 is fixedly secured to the pivoting frame 25 about pivot 26 and is driven by motor 18 and gear drive 19. It may be desired to utilize a plurality of such motors and gear drives, as illustrated in FIG. 8, without any undue complication to the circuitry or mechanics within the purview of the instant invention.

A shut-off arm 28 is fixedly secured to the arcuate gear 27 whereupon actuation of switch "A", the switch "B" is in a first position wherein frame 25 is in an "open position", as illustrated by the solid arrows in FIG. 3, and accordingly electrical current will flow through switch "A", switch "D", terminal 7, terminal 8, terminal 5, terminal 4, terminal 3, and directed to motor 18, thereafter directed through terminal 1 and terminal 2 back to battery supply 20 to complete current circuit. Motor 12 turns gear 19, gear 19 turns arcuate gear 27 that lower frame 25. Upon frame 25 striking switch "D" positioned at lowest orientation relative to opening 117, power will be shut off to motor 18. Color lens 13 (or frame 25) will be positioned in alignment with clear lens 12 and overlying the opening 117 subsequent to a welding operation and upon an operator's desiring to open lens 13, the operator merely actuates switch "B" to the second or dotted position as illustrated in FIG. 3. By repositioning of the operator's chin (FIG. 5), the electric current will be directed from the batteries 20, through switch "A", switch "C" and terminal 9, terminal 8, terminal 5, terminal 6, terminal 1 to motor 18 whereupon the motor will reverse polarity, as illustrated in the phantom polarity reversal designation, and flow from motor to terminal 3, terminal 2 which is again back to battery source. Motor 18 turns gear 19 in an opposite direction, gear 18 turns arcuate gear 27 and lifts frame 25 opening, when frame 25 completing its upward movement, the shut off arm 28 which mounts on arcuate gear will strike switch "C" and cut off power to motor 18.

The manner of usage and operation therefore of the instant invention should be apparent from the above description, and accordingly no further discussion relative to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An improved welding hood formed with a viewing window for use by an operator to include electric power for manipulating a first lens relative said viewing window by an operator's chin, said welding hood comprising, a framework integrally secured exteriorly of said welding hood, and said framework including an opening in alignment with said viewing window, and motor means including a drive means mounted within said framework to manipulate said first lens from a first position removed from said viewing window and said opening to a second position aligned with said viewing window and said opening, and first electrical switch means positioned interiorly of said welding hood for actuation by said operator's chin for moving said first lens from said second position to said first position, and wherein a second switch is positioned within said framework for actuating said first lens from said first position to said second position, and wherein said drive means includes a rotatable pinion gear mounted to said motor means and a rack mounted to said lens, and further including a third switch positioned interiorly of said hood and positioned adjacent to and cooperating with said rack to de-energize said motor wherein said rack is integrally secured to said first lens, and said first lens is positioned to said third switch when said viewing lens is in said second position, and wherein a fourth switch is positioned in alignment and underlying said third switch engageable by said rack to de-energize said motor when said first lens is repositioned from said second position to said first position, and wherein said first lens pivots relative to said opening and is mounted to an arcuate gear engageable by said motor means and said arcuate gear includes an integrally secured shut-off arm to engage said third switch when said first lens is in said first position and said first lens pivotal to said second position to engage said fourth switch, and wherein said second switch is a triple pole double throw switch.

* * * * *